(12) United States Patent
Leitner

(10) Patent No.: US 6,221,196 B1
(45) Date of Patent: Apr. 24, 2001

(54) METHOD FOR IMPROVING THE ADHESION OF AN ELASTOMERIC, POLYMERIC MATERIAL TO A SUPPORT ELEMENT

(75) Inventor: Helmut Leitner, Hemsbach (DE)

(73) Assignee: Firma Carl Freudenberg, Weinheim (DE)

( * ) Notice: Subject to any disclaimer, the term of this patent is extended or adjusted under 35 U.S.C. 154(b) by 0 days.

(21) Appl. No.: 09/291,591

(22) Filed: Apr. 8, 1999

Related U.S. Application Data
(60) Provisional application No. 60/081,702, filed on Apr. 14, 1998.

(30) Foreign Application Priority Data

Apr. 8, 1998 (DE) .............................................. 198 15 758

(51) Int. Cl.[7] ...................................................... C09J 5/02
(52) U.S. Cl. .................................. 156/307.5; 106/287.11; 156/326
(58) Field of Search ....................... 106/287.11; 156/326, 156/307.5

(56) References Cited

U.S. PATENT DOCUMENTS

| | | | | |
|---|---|---|---|---|
| 2,706,166 | * | 4/1955 | Gurney | 156/307.5 |
| 4,308,071 | * | 12/1981 | Gervase | 156/326 |
| 5,728,203 | * | 3/1998 | Vorse et al. | 106/287.11 |

FOREIGN PATENT DOCUMENTS

| | | |
|---|---|---|
| 216 944 | 1/1985 | (DE) . |
| 0 603 073 | 6/1994 | (EP) . |
| 0 764 687 | 3/1997 | (EP) . |

* cited by examiner

*Primary Examiner*—John J. Gallagher
(74) *Attorney, Agent, or Firm*—Kenyon & Kenyon

(57) ABSTRACT

A method for improving the adhesion of an elastomeric, polymeric material to a support element while being shaped and vulcanized thereon, in which the support element is wetted in the region of the adhesion zone with a liquid composition of an adhesion promoter, the coating thus formed is solidified, and the elastomeric material is subsequently shaped on and solidified by vulcanization, an aqueous and/or alcohol solution of a thiocyanatosilane being used as the adhesion promoter.

14 Claims, No Drawings

METHOD FOR IMPROVING THE ADHESION OF AN ELASTOMERIC, POLYMERIC MATERIAL TO A SUPPORT ELEMENT

This application claims benefit of Provisional 60/081,702, filed Apr. 14, 1998.

BACKGROUND OF THE INVENTION

The present invention relates to a method for improving the adhesion of an elastomeric, polymeric material to a support element while being shaped on and vulcanized, in which the support element is wetted in the region of the adhesion zone with a liquid composition of an adhesion promoter, the coating thus formed is solidified, and the elastomeric material is subsequently shaped on and solidified by vulcanization.

It is known per se to use silanes as adhesion promoters when vulcanizing an elastomeric material onto a support element.

This known procedure does not, however, result in a sufficiently mechanically strong joint between the elastomeric material and the support element with all elastomeric materials. Resins or latices are therefore used for the adhesion of NBR, in order to achieve sufficiently strong adhesion. For practical use in industrial-scale production, this involves considerable complexity.

Thiocyanatosilanes are known per se as additives for use in the manufacture of homogeneous rubber mixtures. Their purpose is to impart better strength to a rubber mixture.

SUMMARY OF THE INVENTION

It is the object of the present invention to describe an adhesion promoter which is simple to use and which guarantees good adhesive strength when sulfur-crosslinked elastomeric materials are utilized.

This and other objects of the invention are achieved by a method for improving the adhesion of an elastomeric, polymeric material to a support element while being shaped on and vulcanized, in which the support element is wetted in the region of the adhesion zone with a liquid composition of an adhesion promoter, the coating thus formed is solidified, and the elastomeric material is subsequently shaped on and solidified by vulcanization, wherein an aqueous and/or alcohol solution of a thiocyanatosilane is used as the adhesion promoter.

DETAILED DESCRIPTION OF THE INVENTION

Thiocyanatosilanes have hitherto not been used at all as adhesion promoters or in the production of adhesion promoters. Surprisingly, they make it possible to achieve extremely good adhesive strength when vulcanizing any sulfur-crosslinked elastomeric material onto a solid object, for example an elastomeric material onto metal. It is important for this purpose to produce an extremely thin and homogeneous film on the support element, which is to the greatest extent possible free of irregularities such as bubbles, variations in film thickness in different areas, and the like. Surprisingly, it is possible with the use of thiocyanatosilanes to meet these requirements without difficulty. It is assumed that the excellent adhesive strength upon subsequent vulcanization of sulfur-crosslinked elastomeric materials is to be attributed to this in particular.

The thiocyanatosilane is advantageously used in dissolved form; the solids content of the solution is to be a maximum of 10 wt % thiocyanatosilane, advantageously less than 5 wt %. In a practical exemplary embodiment which is used in the mass production of shaft sealing rings, the content by weight is 0.8 to 1.0 wt %, advantageously 0.9 wt %. This ensures that what results is a particularly thin and uniform coating of the support elements, for example of the support rings, made of sheet steel, of radial shaft sealing rings. These can have a diameter which begins in the 5-mm category.

The solution can contain a proportion of no more than 50 to 80 wt % alcohol in order to improve film formation homogeneity even further and to prevent irregularities.

Practically any known alcohol can be used as the alcohol, for example methanol, ethanol, propanol, isopropanol, butanols, pentanols, hexanols, and/or mixtures of these various alcohols. The use of ethanol is generally preferred.

The adhesion promoter must be dried gently to ensure that a particularly uniform film is formed. The use of temperatures between 20 and 80° C., advantageously between 40 and 60° C., has proven outstandingly successful.

Particularly good adhesion can be achieved if the adhesion promoter is baked after drying for a period of 5 to 20 minutes at a temperature of 50 to 200° C. Baking is of considerable importance especially for safety-relevant applications, for example for applications in the field of support bearings for machines and devices, and with respect to the adhesion of rubber sealing lips to a sealing ring which is used in shock absorbers, wheel bearings, or in the hydraulic field.

If an aqueous solution is used to constitute the adhesion promoter layer, it has proven to be advantageous if the solution used is acidified. Any acid can, per se, be used. The use of acetic acid has proven particularly advantageous. The strength with which sulfur-crosslinked vulcanisates adhere can be improved if aminosilanes are present in the thiocyanatosilane. The concentration in this context should be no more than 50 wt %; in practical application, it is generally in the range of 0.2 wt %.

The present invention will be explained further below with reference to Examples.

EXAMPLE 1

Following prior degreasing, a strip of sheet steel was dipped into an aqueous solution of a thiocyanatosilane and then dried. The solution had the following composition:

| | |
|---|---|
| Water | 25 wt % |
| Ethanol | 74 wt % |
| Acetic acid | 0.1 wt % |
| Thiocyanatosilane | 0.9 wt % |

After removal, the strip was dried at a temperature of 50° C. for a period of 30 minutes, and then transferred into a baking chamber for a period of 20 minutes. The temperature in the baking chamber was 175° C. Subsequent thereto, a rubber element was shaped onto the strip using a vulcanization tool, and by subsequent vulcanization was solidified and joined to the strip. The rubber material used had the following composition:

| | |
|---|---|
| Nitrile-butadiene rubber (NBR) | 30 wt % |
| Carbon black | 30 wt % |
| Silicates | 30 wt % |
| Processing auxiliaries | 3 wt % |
| Antioxidants | 2 wt % |
| Plasticizers | 2 wt % |
| Vulcanization chemicals | 3 wt % |

The vulcanization temperature was 190° C., and vulcanization time was 4 minutes.

Following vulcanization, the composite part was removed from the vulcanization tool, cooled, and the strength of the resulting joint between the shaped rubber element and the strip was measured. The specific adhesive strength was 11 N/mm$^2$. The resulting tear zone was located within the rubber element. The surface of the sheet-metal strip was thus still covered with rubber after the rubber element had been torn off.

EXAMPLE 2

The experiment above was repeated, the adhesion promoter coating being produced using an aqueous solution which instead of alcohol contained traces of acetic acid. The acetic acid content was approximately 0.2 wt %. The specific adhesion strength of the joint was somewhat better than indicated above, specifically 12 N/mm$^2$.

Tiny defects were visible to the naked eye in the region of the breakage zone.

EXAMPLE 3

The procedure described in Example 1 was repeated, except that in addition to the thiocyanatosilane, a concentration of 0.2 wt % (in terms of the solids content) of an aminosilane was added to the mixture. The compound was entirely defect-free, and adhesive strength was 13 N/mm$^2$.

EXAMPLE 4

The procedure as described in Example 1 was repeated, with the difference that the thiocyanatosilane was replaced by 4,4,15,15-tetraethoxy-3,16-dioxa-8,9,10,11-tetrathio-4,15-disi lanooctadecane, as obtainable, for example, under the commercial designation SI 69. The specific adhesion strength of the joint was 1.3 N/mm$^2$, and was thus totally insufficient for higher-grade applications.

What is claimed is:

1. A method for improving the adhesion of an elastomeric, polymeric material to a support element while being shaped on and vulcanized, comprising the steps of: wetting a support element in a region of the adhesion zone with a liquid composition of an adhesion promoter to form a coating, solidifying the coating thus formed, and subsequently shaping and solidifying the elastomeric material by vulcanization thereon, wherein the adhesion promoter is an aqueous or alcohol solution of a thiocyanatosilane.

2. The method as defined in claim 1, wherein a maximum of 10 wt % of the thiocyanatosilane is present in the solution.

3. The method as defined in claim 1, wherein a maximum of 50 to 96 wt % alcohol is present in the solution.

4. The method as defined in claim 2, wherein a maximum of 50 to 96 wt % alcohol is present in the solution.

5. The method as defined in claim 1, wherein the alcohol is selected from the group consisting of methanol, ethanol, propanol, isopropanol, butanols, pentanols, hexanols and mixtures thereof.

6. The method as defined in claim 1, wherein the adhesion promoter is dried at a temperature of 20 to 80° C. after its application.

7. The method as defined in claim 6, wherein the adhesion promoter is dried at a temperature of 40 to 60° C. after its application.

8. The method as defined in claim 1, wherein the adhesion promoter is baked at a temperature of 50 to 200° C. for a period of 5 to 20 minutes after drying.

9. The method as defined in claim 1 wherein an acidified aqueous solution is utilized.

10. The method as defined in claim 9, wherein the solution is acidified using acetic acid.

11. The method as defined in claim 1, wherein the adhesion promoter also includes at least one aminosilane.

12. The method as defined in claim 11, wherein the proportion of aminosilane in terms of the solids content of the mixture is a maximum of 5 wt %.

13. The method as defined in claim 9, wherein the concentration of acid is no greater than about 0.2 percent by weight.

14. The method as defined in claim 10, wherein the concentration of acetic acid is no greater than about 0.2 percent by weight.

* * * * *